(12) United States Patent
Steinhaus et al.

(10) Patent No.: US 6,546,292 B1
(45) Date of Patent: Apr. 8, 2003

(54) HIGH IMPEDANCE, LOW POLARIZATION CARDIAC ELECTRODE

(75) Inventors: Bruce M. Steinhaus, Flagstaff, AZ (US); Louis J. Smith, Flagstaff, AZ (US); William H. Wiley, Flagstaff, AZ (US); Robert C. Krall, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/185,995

(22) Filed: Nov. 4, 1998

(51) Int. Cl.[7] ............................................. A61N 1/05
(52) U.S. Cl. ..................... 607/116; 607/121; 607/122; 600/373; 600/374; 600/395
(58) Field of Search ................................. 607/121, 122, 607/129, 119, 116; 600/374, 373, 372, 395

(56) References Cited

U.S. PATENT DOCUMENTS

| | | | | |
|---|---|---|---|---|
| 4,011,861 A | * | 3/1977 | Enger | 607/121 |
| 4,187,390 A | * | 2/1980 | Gore | |
| 5,269,810 A | * | 12/1993 | Hull et al. | 607/129 |
| 5,318,572 A | * | 6/1994 | Helland et al. | 607/121 |
| 5,405,373 A | * | 4/1995 | Petersson et al. | 607/121 |
| 5,560,986 A | * | 10/1996 | Mortimer, Jr. | 174/110 FC |
| 5,683,443 A | * | 11/1997 | Munshi et al. | 607/121 |
| 5,755,762 A | * | 5/1998 | Bush | 607/121 |
| 6,080,151 A | * | 6/2000 | Swartz et al. | 606/45 |
| 6,218,000 B1 | * | 4/2001 | Rudolf et al. | 264/122 |

* cited by examiner

Primary Examiner—Kennedy Schaetzle
(74) Attorney, Agent, or Firm—Wayne House (57) ABSTRACT

A layered electrode having a large tissue contact area of the portion of the electrode that is electrically active and providing low polarization losses, high pacing impedance and low chronic stimulation voltage. In a fundamental embodiment, the electrode tip has an outer layer of microporous material which is permeable to conductive body fluids which covers a layer of insulating material which is provided with at least one perforation through the thickness of the material. The at least one perforation provides a localized, high current density path. Both of these layers in turn cover the exterior surface of an electrically conductive, preferably metal, electrode body. The present invention is, in a preferred embodiment, a multiple layered device having, in sequence, a) an external layer promoting tissue attachment, b) a cell exclusion layer, which prevents tissue ingrowth into the subsequent underlying layers while allowing passage of conductive fluids, c) a third layer of substantially electrical insulating material with selected or tailored perforations or through holes which provide high current density paths, d) a fourth layer that contains a electrically conductive material of high surface area and e) a fifth metallic layer of a high surface area electrode.

45 Claims, 10 Drawing Sheets

HIGH IMPEDANCE, LOW POLARIZATION CARDIAC ELECTRODE

BACKGROUND OF THE INVENTION

1. Field of Invention

This invention relates to implantable electrodes and more particularly to a cardiac pacing lead distal tip electrode.

2. Description of Related Art

Pacemaker leads are used to electrically connect a cardiac pacemaker pulse generator to heart tissue to be stimulated. For example, endocardial type leads which are inserted into a vein and then guided into the desired heart cavity include at their distal end an electrode tip designed to contact the endocardium or the tissue forming the inner lining of the heart. These leads, connected to a pacemaker, are commonly used for both sensing electrical signals produced by the heart and providing pacing stimulation.

The electrical pacing signal that is delivered to the cardiac muscle must be of sufficient magnitude to depolarize the excitable cells that are adjacent to the electrode tip. The electrode size and shape, tissue conductivity, and the distance separating the electrode tip from the excitable cells are factors in determining the stimulus threshold. Many of these factors are highly determined by the geometry and material composition of the electrode.

The duration or battery life of a pacemaker is, in part, dependent on the current drain that is used in stimulating the cardiac muscle. This current drain is determined by the programmed voltage, pulse width, the rate of the pacemaker stimulator and the pacing impedance presented to the pulse generator. It is important to note that improvements in pacemaker longevity due to increased pacing impedance are not dependent upon reprogramming the pacemaker in any manner.

The pacing impedance is a function of the macroscopic surface area of the electrode. As it is optimal to have a high pacing impedance, most modern pacing electrode designs strive for a reduced area stimulus electrode. Thus, small diameter electrodes will reduce the stimulus current necessary to pace the heart and will extend the life of the pacemaker. Electrodes having very small tip surface areas, in some designs, are problematic in that the small surface area or sharp point can increase the chance of the electrode perforating the ventricular wall, which can lead to blood loss into the pericardial sack. In addition, small tip electrodes are also very sensitive to implantation angle and can demonstrate marked stimulus threshold variability during occurrences of lead micro-dislodgement due to the very uneven surface structure of the endocardial wall. At times the sensitivity to stimulus threshold with micro-dislodgment can cause exit block or complete loss of cardiac stimulation.

It should also be noted that electrodes having very small stimulus areas are prone to generate large polarization artifact signals. These voltage signal distortions are inefficient in that they take energy away from stimulation of the cardiac tissue. More importantly, these artifact signals can present problems to the pacemaker in sensing the following heart activity. One method to reduce this artifact is to increase the microscopic surface area of the electrode, while keeping the macroscopic surface area fixed. This microscopic surface area is the sum of all the microscopic cracks, crevices and indentations on the surface of the electrode.

The electrode must also provide a means for sensing the electrical activity or signal of the heart. The ability to efficiently detect heart activity is directly related to the sensing impedance of the electrode. Optimal sensing occurs with low sensing source impedance electrode designs. Thus large macroscopic surface area electrodes are desired for sensing.

The pacing, or stimulating, threshold is a measurement of the energy required for a voltage pulse to initiate a contraction in the heart tissue. The stimulus threshold typically rises after implantation of an electrode since there is an increase in the spacing between the electrode tip and the excitable cardiac tissue. This is a typical foreign body tissue healing response to the electrode tip and this healing response includes the generation of a fibrous capsule around the electrode tip. Lower stimulus thresholds have resulted from electrode designs with a porous structure at the distal electrode end. Optimal porous structures appear to minimize the initial foreign body reaction and hasten the subsequent healing response to the pacemaker lead tip electrode.

Thus, a considerable design challenge in current state-of-the-art electrodes is the optimization of the electrode surface area, geometry and porosity. High pacing impedance is optimally achieved by low macroscopic surface area electrode geometry. Low polarization losses are optimally achieved by a high microscopic surface area electrode geometry. Low sensing source impedance requires large macroscopic surface area electrode geometry. Low sensitivity to micro-dislodgement requires large macroscopic surface area electrode geometry. The design outcome is always a compromise between the opposite desired extremes. Recent devices utilize various types of surface coatings or metal surface enhancements (e.g., iridium oxide). These surface changes increase the microscopic surface area while keeping the electrode macroscopic surface area relatively the same. These surface enhancements help reduce the polarization losses for a given tip geometry but do not fully solve the design tradeoff concerns on the electrode surface.

An electrode tip design, taught in U.S. Pat. No. 3,476,116 by Parsonnet et al., utilizes an electrode tip with a fluid filled cavity. Within this cavity is a high surface area electrode. The fluid filled cavity is isolated from the tissue to be stimulated by an electrically insulating material containing a small aperture. This electrode tip design has, in effect, a large electrode surface area which lowers the polarization losses. The tissue to be stimulated however perceives a very small surface area due to the small aperture, resulting in high tip to tissue impedance. This design performed reasonably well short term, however the long term or chronic performance was shown to be compromised. The small aperture of the Parsonnet design was highly sensitive to lead movement due to micro-dislodgment which changed the interface between the tissue and the small aperture. This aperture dislodgment caused high stimulation voltage thresholds in some patients and in extreme cases caused total electrode exit block which is a complete failure to stimulate.

A modified Parsonnet design was disclosed by F. Hoffmann in an article entitled "Stimulating Electrode With Low Energy Consumption" (*Medical and Biological Engineering,* September 1973, Pg. 659–660). This proposed design added additional holes or apertures to the original Parsonnet design. The sensitivity of the tip to tissue interface was effectively reduced, however consistent and stable chronic pacing thresholds were still not obtained.

A similar electrode tip design is disclosed in U.S. Pat. No. 5,282,844 to Stokes et al. To achieve low polarization losses, Stokes et al. teach the use of a fluid filled cavity containing an electrode with a large surface area, similar to that of Parsonnet et al. Low stimulation voltage thresholds are achieved by the use of a cavity sheath with a small aperture, again similar to the Parsonnet design. To overcome the chronic increase in stimulation voltage, the Stokes design incorporates a steroid eluting device contained within the bodily fluid filled cavity. The steroid elution alters the results of the reaction to the foreign body response at the electrode tip to tissue interface and results in low chronic stimulation voltage thresholds.

In U.S. Pat. No. 4,011,861, Enger teaches the use of an electric terminal, with a porous outer sheath. The porous sheath encourages the ingress of blood vessels without the production of a fibrous tissue interface which would result in high stimulation voltages. The large number of pores result in a large number of sites of current loss with no areas of high current density nor a marked increase in stimulus pacing impedance.

MacGregor teaches in U.S. Pat. No. 4,281,669 a high surface area, sintered metal electrode tip, incorporating an outer porous polymeric covering. The pores provide for an improved tissue ingrowth structure at the tip. The high surface area sintered metal electrode provides low polarization losses. Similar to Enger, the large number of pores of MacGregor result in no areas of high current density for stimulation.

In U.S. Pat. No. 5,090,422 to Dahl et al., an electrode sheath is disclosed. Dahl et al. teach the use of a porous polymeric sheath, which when impregnated with bodily fluids, becomes electrically conductive. U.S. Pat. No. 5,609,622 to Bush also discloses a porous polymeric sheath. This polymeric sheath has a pore size of less than 10 microns for the purpose of precluding tissue attachment which facilitates removal of the lead after chronic implantation. The porosity also allows bodily fluids to impregnate the sheath thereby allowing electrical energy to pass through the sheath. The porous polymeric sheaths disclosed in Dahl et al. and Bush result in a large number of very small sites of current loss with no areas of high current density nor a marked increase in stimulus pacing impedance.

SUMMARY OF THE INVENTION

The present invention provides a layered electrode having an electrically conductive material, covered by one or more layers, wherein the electrode provides high pacing impedance, a low chronic stimulation voltage threshold and low post pacing polarization (artifacts. Specifically, the present invention is an electrode comprising an electrically conductive material which is covered or substantially covered by a layer of substantially electrically insulating material having at least one macroporous perforation (or aperture) therethrough, and a microporous cover over the perforation. The at least one macroscopic perforation provides a high current density path while the microporous cover is permeable to electrically conductive body fluids which allow current to flow through the cover. Preferably the microporous cover simultaneously prevents tissue ingrowth into the at least one perforation.

In a preferred embodiment, the microporous layer is provided as two layers in the form of an external microporous layer having a pore size appropriate to promote tissue attachment to that layer by allowing tissue to grow into the pores of that layer, and an inner cell exclusion layer with pores adequately small to restrict or entirely prevent cell ingrowth. Both layers together are permeable to body fluids. In another preferred embodiment which may be used with either the single or two layer microporous cover, the electrically conductive material of the electrode is in the form of an electrically conductive component provided with a surface of large area such as a porous metal, powdered metal, sintered metal, or any other means of enhancing the surface area of the electrically conductive component in order to enhance the charge transfer between the electrically conductive component and electrically conductive body fluids. The means of enhancing surface area of the electrically conductive material may involve the addition of one or more layers to the surface of the electrically conductive material.

These multiple layers, in concert, can provide good biocompatibility, electrode tip anchoring to the tissue to be stimulated, prevention of cell proliferation into the subsequent layers, one or more localized high current density stimulation sites, a high pacing impedance due to an effectively small macroscopic surface area electrode, and a low post pacing polarization artifact.

BRIEF DESCRIPTION OF THE DRAWINGS

These and other objects and advantages of the present invention may be fully understood and appreciated in conjunction with the attached drawings and following detailed descriptions.

DETAILED DESCRIPTION OF THE DRAWINGS

The present invention is an electrode comprising a layered tip which provides a chronic electrode to tissue impedance of greater than about 1000 ohms and maintains a chronic stimulation voltage of less than about 5.0 volts without the use of steroid elution. In a preferred embodiment, the present invention is a multiple layered device comprising, in sequence, a) an external layer promoting tissue attachment, b) a secondary cell exclusion layer, which prevents tissue ingrowth into the subsequent layers, while allowing passage of conductive fluids, c) a third layer of substantially electrical insulating material with selected or tailored perforations, apertures or through holes which provide high current density paths, d) a fourth layer that contains a electrically conductive material of high surface area and e)

a fifth metallic layer having a high surface area. "Comprising in sequence" is hereby defined as a specific order or arrangement of the layers but does not preclude the use of additional intermediate layers. Thus, for example, the tissue attachment layer may be physically separated from the cell exclusion layer by a mesh material. The addition of this mesh, or intermediate layer, therefore does not preclude the tissue attachment layer from being in sequence with the cell exclusion layer. The term "cover" is hereby defined as a surface or material which, at least partially, overlays, envelops, coats or otherwise covers an underlying or internal surface or material. Similar to the above definition of "comprising in sequence", an internal surface or material is considered covered, despite the presence of any additional surface or materials between the cover and the internal covered surface or material. To be considered covered, an internal surface or material does not have to be in direct contact with the cover. For example, intermediate layers or surfaces may exist between the covered surface and the cover.

A unipolar pacing lead, as generally described previously, is an implantable insulated electrical wire terminating in a distally located electrode. The electrical current path is composed of both conduction through the pacing lead electrical wire which is considered electronic flow (the flow of electrons) and conduction through the blood and other body fluids which is considered ionic flow (the flow of ions). The transition from electronic conduction to ionic conduction requires a charge transfer across the electrode surface interface. The surface of the electrode is therefore the physical area or interface where such a charge transfer occurs.

Figure 1:
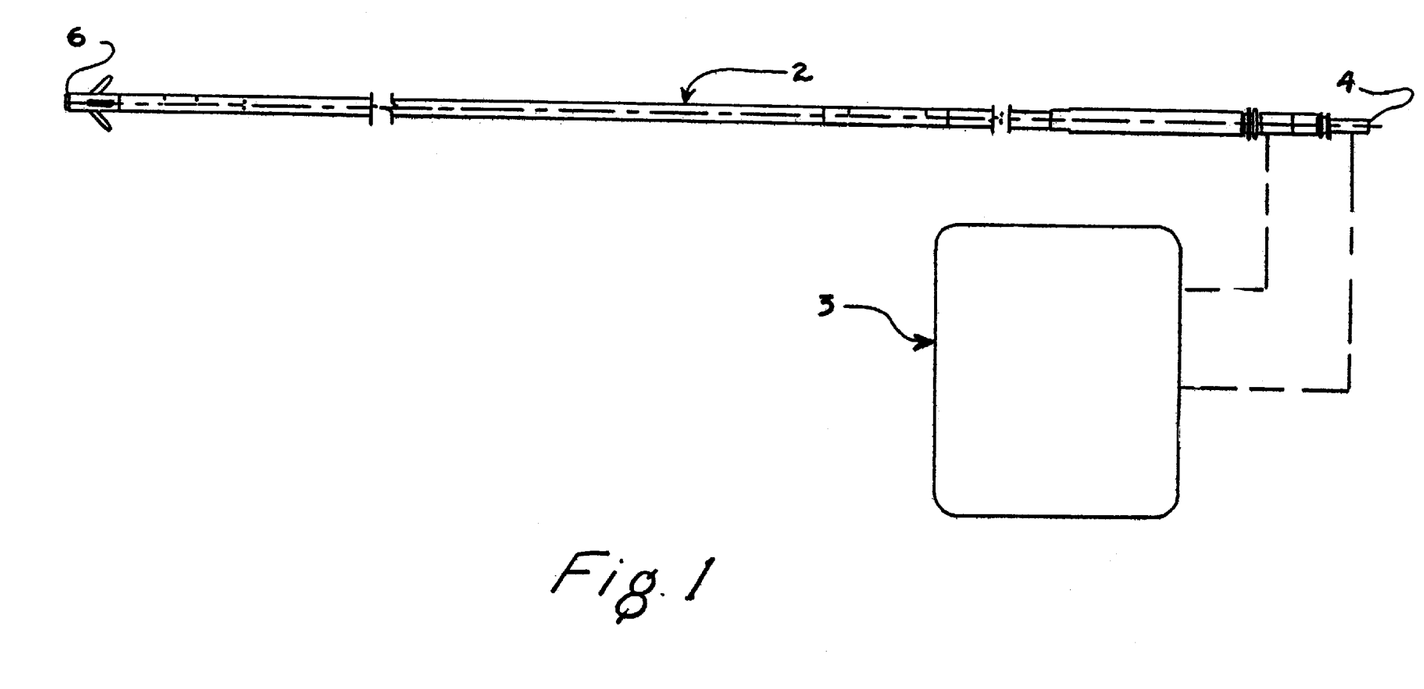
FIG. 1 shows an overall view of a pacing lead and stimulation system of the present invention.

FIG. 1 is a plane view of a typical implantable pacing lead 2. The pacing lead 2 has a proximal end 4, configured to connect to a pacing generator, or stimulator 3 and a distal electrode 6 for stimulation of bodily tissue. The implantable lead 2 and the stimulator 3, comprise a stimulation system.

Figure 2:
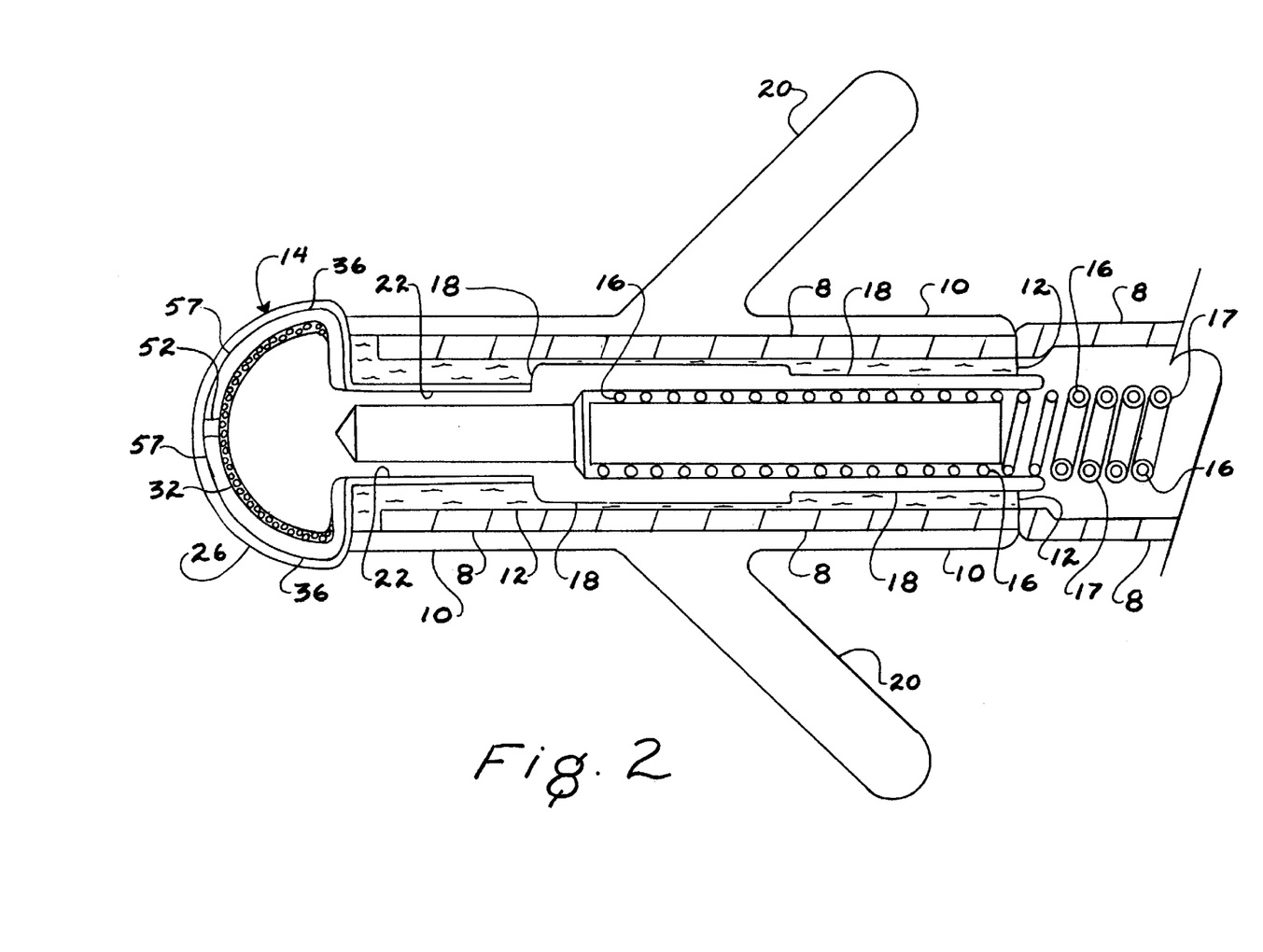
FIG. 2 shows a longitudinal cross section of the multiple layered distal electrode of the present invention.

FIG. 2 is a longitudinal cross section of the distal electrode 6. The coiled electrical conductor 16 is electrically connected to the base electrode 18. The coiled electrical conductor 16 is contained within an outer sheath 8. Electrical isolation is, in a preferred embodiment, achieved by coating the coiled wire 16 with an electrically insulating coating 17, for example ethylene-tetrafluoroethylene (ETFE). At the extreme distal end, the outer sheath 8 is covered by anchoring tine component 10 which incorporates anchoring tines 20. The outer sheath 8 is attached to the base electrode 18 by a bonding agent 12. The same bonding agent 12 is used to attach the multiple layers of the distal electrode assembly 14 to the base electrode 18. The outer sheath 8 can be fabricated from any suitable biocompatible material, for example, polyurethanes, silicones or in a preferred embodiment porous polytetrafluoroethylene. The bonding agent 12 can be any suitable biocompatible material such as silicone or in a preferred embodiment fluorinated ethylene propylene (FEP). A suitable form of FEP is available from Norton Performance Plastics, Wayne N.J., as Korton FEP Fluoropolymer Film. The base electrode 18 can have ridges, barbs, grooves or a suitable rough exterior surface finish to enhance the adherence of the bonding agent 12. Similarly, the multiple layers of the distal electrode tip assembly 14 can be configured with appropriately roughened surfaces to increase the adhesive bond strength in the layer to base electrode attachment area 22.

As further shown in FIG. 2, the distal electrode tip of base electrode may be provided with a means for more effective electrical charge transfer in the form of a high surface area coating 32 such as a powdered or sintered metal coating or a coating of other porous or roughened metal. Layer 36 in the form of a perforated sheet of substantially electrically insulating material covers the high surface area coating 32 of the distal electrode tip of base electrode 18. This perforated layer 36, provided with at least one perforation or aperture 52 therethrough surrounded by substantially electrically insulating material 57, is in turn covered by microporous layer 26 which is permeable to electrically conductive body fluids. Aperture 52 provides a localized, high density current path through perforated layer 36.

Perforated layer 36 may simply be captured or contained by an external microporous layer 26, thus a perforated layer 36 does not necessarily have to be directly bonded to the base electrode 18. Multiple layers of the distal electrode tip assembly can be contained in such a fashion.

Figure 2A:
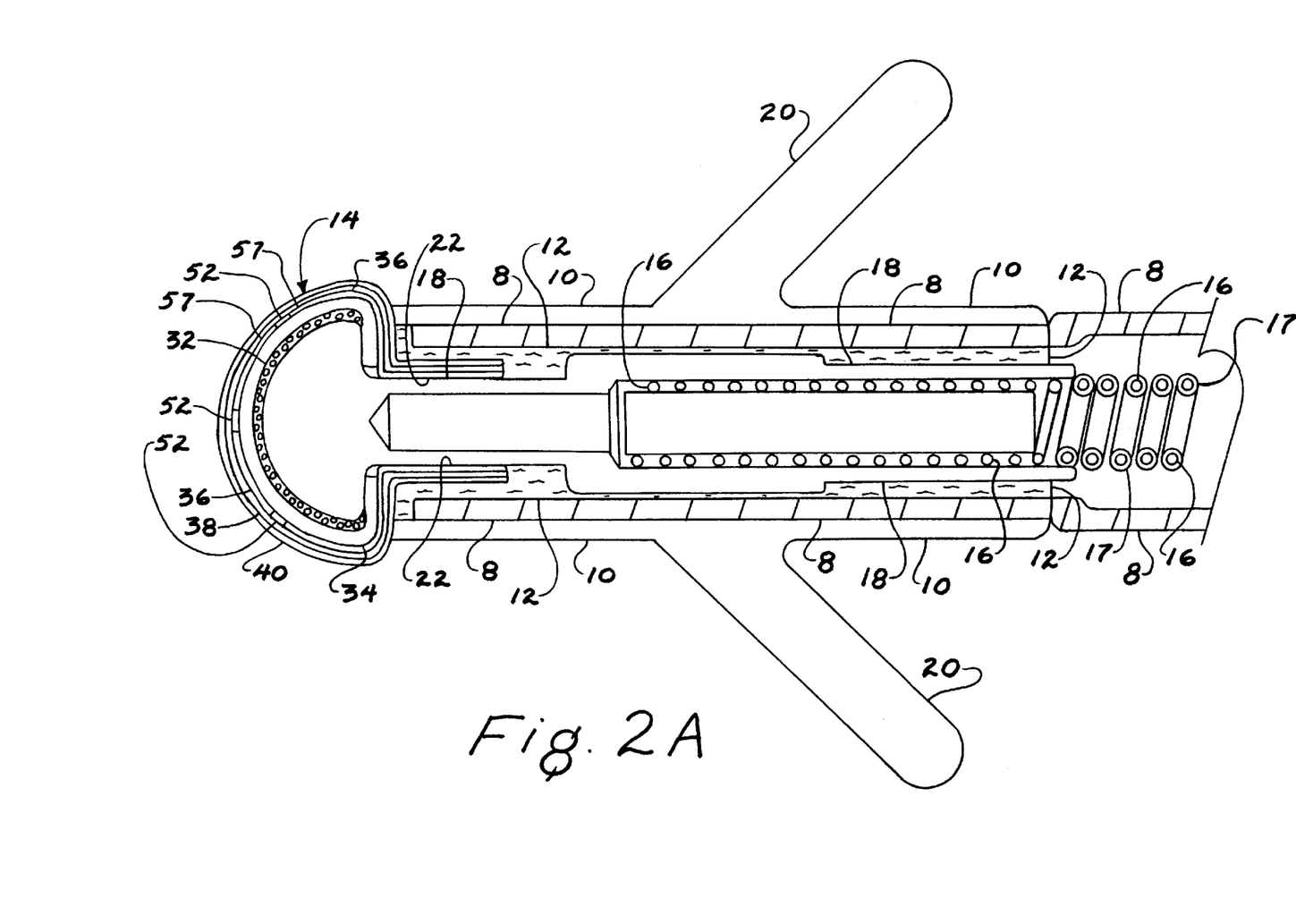
FIG. 2A shows a longitudinal cross section describing a preferred embodiment of FIG. 2 having additional layers.
Figure 3:
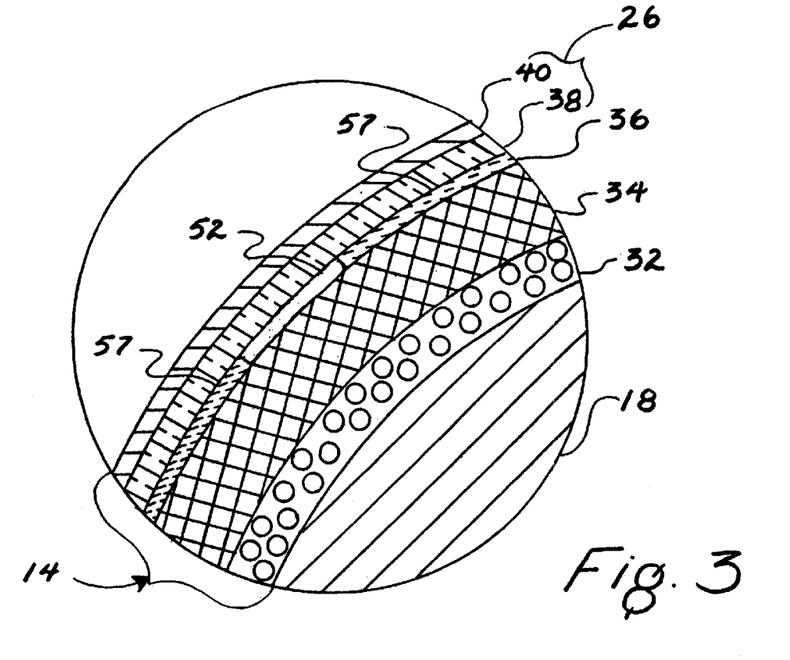
FIG. 3 shows a detailed cross section of the sequenced multiple layers of the distal tip of the present invention.

Shown in the longitudinal cross section of FIG. 2A and in greater detail in the enlarged longitudinal cross section of FIG. 3 is a description of the multiple layer distal electrode assembly 14, wherein wherein the electrically conductive material of base electrode 18 is provided with enhanced surface area by a coating of sintered metal 32 and an additional layer of carbon-filled ePTFE 34. This assembly is then covered with a layer 36 of substantially electrically insulating material having at least one perforation therethough, which is in turn covered by body fluid permeable, microporous layers 38 and 40 wherein layer 38 is a cell exclusion layer and layer 40 is a cell ingrowth layer.

As noted above, the base metallic electrode 18 preferably has an external, selective surface coated with high surface area sintered metal 32. The base metallic electrode 18 can be fabricated from any suitable biocompatible electrically conductive material, or conductive metal element, such as 90%/10% Pt/Ir. The high surface area sintered metal 32 can consist of any conductive biocompatible material having a suitably high surface area. Typical sintered materials 32 include 90%/10% Pt/Ir alloy micro spheres, approximately 20–50 microns in diameter, coated onto the base electrode 18 by conventional means. Adjacent to the high surface area coating 32 is an electrically conductive material, or carbonized polymer, which in a preferred embodiment is a carbon filled ePTFE layer 34. Thus layer 34 comprises an electrically conductive polymer material. This carbon filled ePTFE layer 34 enhances the transfer of electron current flow in the coiled conductor, to ionic current flow of bodily fluids. The high efficiency is a result of the high microscopic surface area of the carbon filled ePTFE in contact with bodily fluids. This carbon filled layer or material is produced in accordance with U.S. Pat. No. 5,560,986 to Mortimer, herein incorporated by reference. In a preferred embodiment, this carbon-filled material is produced following example #1 of the aforementioned patent, with the following exceptions: 1) the tape was calendered through heated rolls to 0.14 mm vs. 0.28 mm, 2) the tape was stretched in the machine direction once vs. twice, with an expansion ratio of 2.5 to one, 3) the expanded tape was then not compressed vs. being compressed. The high surface area of the combined carbon filled layer 34 along with the high surface area of the sintered metal base electrode coating 32, result in low current densities and low polarization losses.

As shown in FIG. 3, a third layer or cover 36 covers the electrically conductive polymer material or the carbon filled ePTFE layer 34. The third layer 36 is fabricated from any suitable biocompatible, substantially electrically insulating material, and is provided with at least one aperture 52 therethrough. In a preferred embodiment layer 36 is FEP with multiple through holes, forming a specific array or pattern of perforations or apertures. This third layer 36, covers and electrically isolates the carbon filled ePTFE layer 34 from the body, except for the current paths provided by the perforations. The precise perforation hole pattern is designed to result in localized areas of high current densities and high electrode pacing impedance. Specific details relating to the construction of this electrically insulating layer or cover are disclosed in subsequent sections. Importantly, the electrically insulating material of this layer is not limited to a near ideal, or high resistance material, and can be formed from a substantially electrically insulating material. A substantially electrically insulating material is hereby defined as a material or layer, which when fully wetted, has an electrical resistance at least about twenty times greater without perforations than with perforations. Thus the goal of the perforations is to achieve localized areas of high, or increased, current densities at the perforation sites compared to the current densities at the non-perforated sites. An aperture is hereby defined as a hole, perforation or a porous area through the thickness of a layer of substantially electrically insulating material (i.e., therethrough) which covers an electrically conductive component, resulting in a high current density at the local site of the aperture.

The fourth layer or cover of the present invention serves as a cell exclusion layer 38. In a preferred embodiment, the cell exclusion layer 38 is formed from ePTFE having a specific microstructure designed to prevent cellular penetration into the inner layers. Cellular ingrowth into the internal layers has the possible negative effect of degraded electrical performance. In a preferred embodiment, the cell exclusion layer or cover is comprised of a thin, high strength, stretched, non-woven web of polytetrafluoroethylene composed substantially of fibrils in which the nodes are represented primarily only as fibril junctions. This layer has a mean fibril length of less than about 3.0 microns with a preferred range of less than about 1.0 microns and more preferably between about 0.05 and 0.4 microns. The thickness of the material is, in a preferred embodiment, between about 1 micron and about 25 microns.

The fifth layer, cover 40, is configured to encourage cell ingrowth or attachment to facilitate the electrode tip anchoring and thus insure consistent chronic electrical characteristics. This cell ingrowth layer or cover 40 is formed, in a preferred embodiment, from ePTFE having a specific microstructure designed to encourage cellular penetration. Preferably, the materials for the cell exclusion layer 38 and the material for the cell ingrowth layer 40 are a laminate of at least two layers of porous polytetrafluoroethylene materials each having a different porosity. The lamination of these two film layers, the process for which will be subsequently described, facilitates the handling of the thin films during subsequent processing. Thus the lamination process is not considered to be critical regarding the electrode performance, and may be eliminated if deemed unnecessary.

Figure 3A:
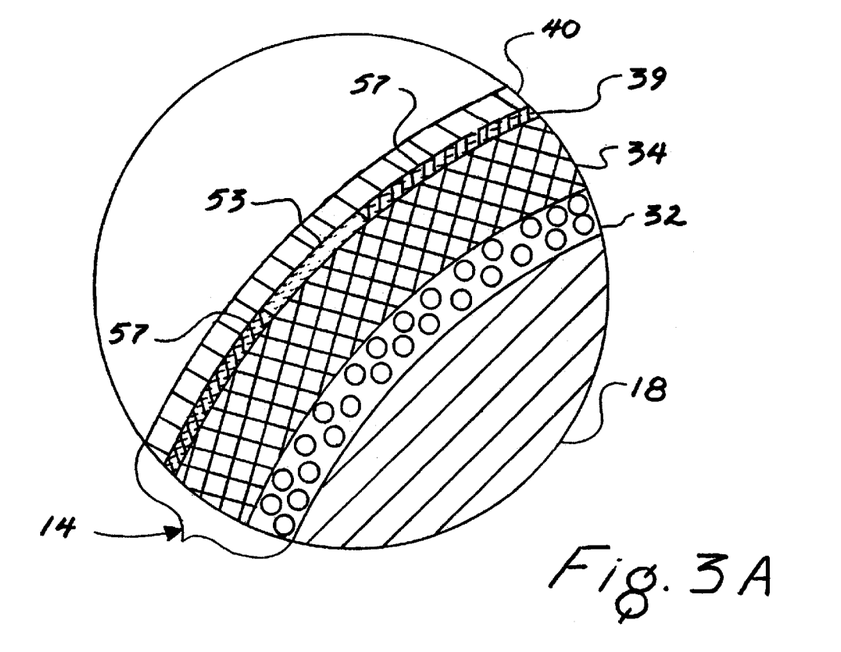
FIG. 3A shows a detailed cross section of sequenced layers in an alternative embodiment of the distal tip of the present invention.

FIG. 3A describes a detailed cross section, in similar fashion to the cross section of FIG. 3, of an alternative embodiment of the inventive electrode tip wherein layer 36 provided with the at least one aperture is combined with microporous layer 26 (preferably intended to exclude cell ingrowth). This can be accomplished in different ways with the result being a layer 39 provided with apertures 53 which are microporous rather than entirely open, with the pore size of the microporous region preferably being adequately small to exclude cell ingrowth. Apertures 53 are surrounded by substantially electrically insulating material 57. Layer 39 is then preferably provided with additional covering layer 40 which is a microporous cell ingrowth layer. Layer 39 is provided over base electrode 18, preferred sintered metal coating 32 and preferred conductive ePTFE layer 34.

Layer 39 may be made in various ways. One method is to select a sheet of microporous ePTFE having the desired mean fibril length appropriate for aperture 53 and densify the area 57 surrounding aperture 53 by the application of pressure until the area 57 is no longer porous. This results in area 57 being of reduced thickness in comparison to the aperture region 53; this reduced thickness is not anticipated to be a problem with respect to the function of this layer. Densification of porous ePTFE to provide selected non-porous regions is taught by U.S. Pat. No. 5,032,445 to Scantlebury et al. Alternatively, non-porous region 57 may be made by filling the void spaces of the porous sheet of ePTFE with a suitable filler such as medical grade silicone adhesive while leaving the aperture region 53 unfilled and still microporous; alternatively this region 57 may be provided with a coating of a non-porous sealant such as the silicone material. All of these methods allow aperture 53 to provide a localized area of high current density.

The portion of the laminate or cover containing the cell ingrowth layer 40 is a porous expanded polytetrafluoroethylene material (ePTFE) having a microstructure of nodes interconnected by fibrils, made in accordance with the teachings of U.S. Pat. Nos. 3,953,566 and 4,187,390 to Gore, both of which are incorporated herein by reference. These patents teach that ePTFE may be manufactured in a range of densities (inversely proportional to porosity) and pore sizes. Pore size with regard to ePTFE is most commonly characterized in terms in mean fibril length which refers to the mean length of fibrils of the material, or more conveniently, the mean distance between adjacent nodes. The ePTFE material for use as the cell ingrowth layer has an mean fibril length greater than about 3.0 microns and preferably greater than about 50 microns. The thickness of the material ranges from about 10 microns to about 1000 microns, preferably about 40–60 microns.

Mean fibril length is measured as taught by U.S. Pat. No. 5,747,128 at col. 6, lines 19–37. Mean fibril length can be estimated with adequate accuracy for most purposes by visual examination of SEM photomicrographs of an ePTFE sample surface by those of ordinary skill in the art.

The preferred method of making the cellular exclusion layer 38 of the laminate or cover utilizes a portion of a method taught by Bacino in U.S. Pat. No. 5,476,589 entitled "Porous PTFE Film And A Manufacturing Method Therefor," which is also incorporated herein by reference. In the Bacino method, after the appropriate polytetrafluoroethylene starting materials are chosen and prepared as a coagulated dispersion of fine powder polytetrafluoroethylene, the coagulated dispersion powders are lubricated with a hydrocarbon extrusion aid, preferably as odorless mineral spirit such as Isopar K (made by Exxon. Corp.). The lubricated powder is compressed into cylinders and extruded in a ram extruder to form tapes. Two or more layers of tape can be stacked together and compressed between two rolls. The tape or tapes are compressed between rolls to an appropriate thickness, e.g. 5 to 40 mils, or so. The wet tape is stretched transversely to 1.5 to 5 times its original width. The extrusion aid is driven off with heat. The dried tape is then expanded, or stretched, longitudinally between banks of rolls in a space heated to a temperature that is below the polymer melting point of 327° C. The longitudinal expansion is such that the ratio of speed of the second bank of rolls to the first bank is between 10 to 1 and 100 to 1, preferably 35 to 1. The longitudinal expansion is repeated at a ratio greater than 1 to 1 and less than 1.5 to 1, utilizing a third set of rollers.

After the longitudinal expansion, the tape is expanded transversely at a temperature that is less than 327° C. to at least 1.5 times and preferably to 6 to 15 times the input width of the original extrudate while restraining the membrane from longitudinal contraction. While still under constraint, the membrane is preferably heated to above the polymer melting point of 327° C. and then cooled.

Lamination of these two different porous polytetrafluoroethylene materials (the cell ingrowth layer and the cell exclusion layer) is performed by combining some of the steps of the above referenced Bacino method. To perform the lamination, the cell ingrowth material is joined with the material from the Bacino method between the second and third set of rolls and longitudinally expanded together during the above described second longitudinal expansion having an expansion ratio of greater than 1:1 and less than 1.5:1. The thickness of the laminate can be less than 55 microns.

Next the laminate or cover, after the longitudinal expansion, is expanded transversely at a temperature that is less than 327° C. to at least 1.5 times and preferably to 6 to 15 times the input width of the original laminates while restraining the laminate from longitudinal and transverse contraction. While still under constraint the laminate is preferably heated to above the polymer melting point of 327° C. and then cooled.

Figure 4A:
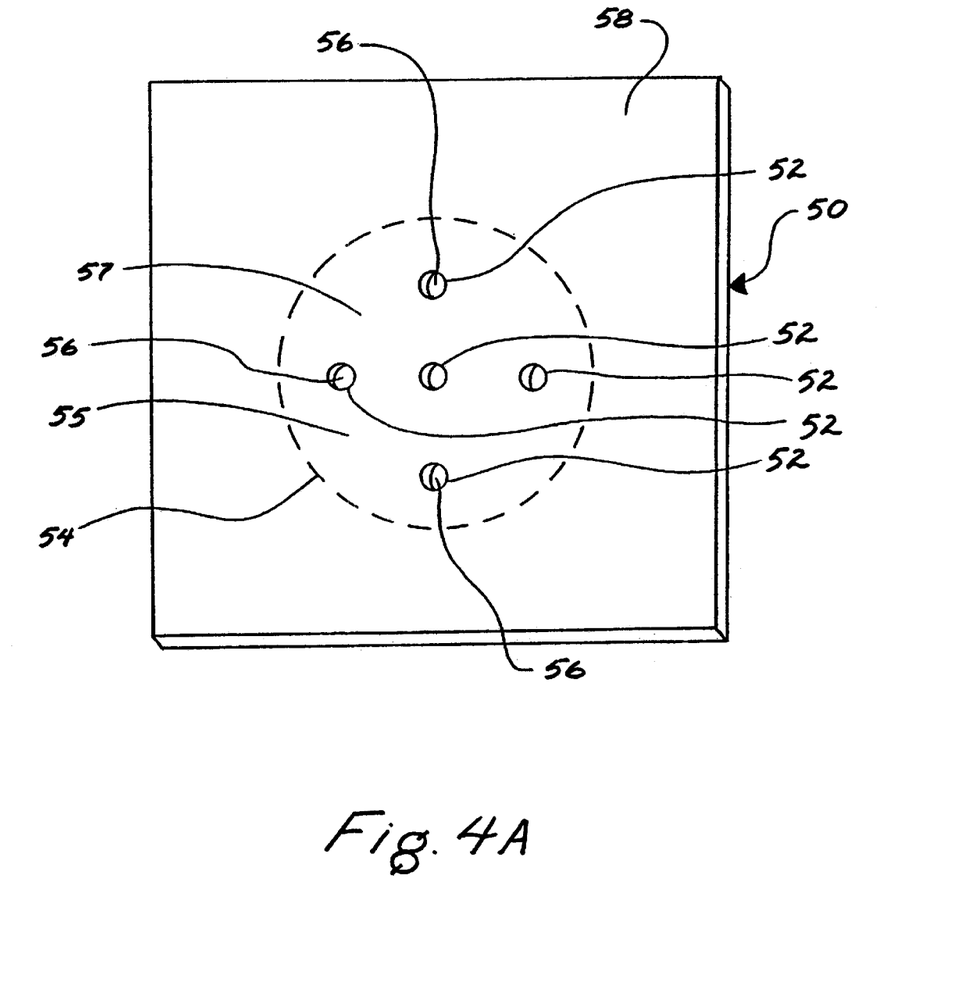
FIG. 4A shows a perspective view of the third, perforated layer of the distal electrode, the layer having at least one aperture therethrough.

The construction of the perforated, substantially electrically insulating layer 36 of FIGS. 2–3 are further described in detail beginning with FIG. 4A. As shown in FIG. 4A, an initial sheet 50 of the substantially insulating material is positioned, in a preferred embodiment, onto a laser cutting fixture (not shown). The substantially insulating layer 50 is then perforated with a series of holes (apertures) 52 surrounded by substantially electrically insulating material 57. The initial sheet 50 has an approximate electrode surface area contained or defined by the periphery 54. This periphery 54 defines an initial maximum surface area or mechanical contact area 55 (the entire area within periphery 54), which covers the entire macroscopic surface area of the sintered metal layer 32 (FIG. 3). Enough material 58 outside of periphery 54 must be provided for attachment of the layer 50 to the electrode assembly as will be seen subsequently in FIG. 6. Each hole 52, has, in a preferred embodiment, a substantially similar hole area 56. After cutting the holes in sheet 50, the ratio of the number of holes 52 multiplied by the typical hole area 56, to the mechanical contact area 55 is preferably less than 0.40. This ratio is referred to as the perforation ratio. Devices of the present invention have typical hole, aperture or perforation areas 56 ranging from about 0.008 to 0.09 mm$^2$ (corresponding to diameters of about 0.1 mm to 0.34 mm for circular apertures) with a preferred range of 0.015 to 0.07 mm$^2$. Devices of the present invention have a preferred number of perforations or apertures 52, ranging from 3 to 30 (at least 3 apertures representing a "multiplicity" of apertures), with a preferred range of 5 to 18. By perforating the insulating sheet 50 while in the flat or planar state, very accurate holes can be cut, having precise hole areas, hole spacing and hole patterns. These high cutting accuracies are difficult to achieve when the insulating layer is in the final hemispherical shape as shown by assembly 14 in FIG. 2. In addition, by only exposing the insulating layer to the cutting process, the other inner and outer layers of the distal electrode tip are not affected or compromised by the perforation cutting operation.

It is important to note that following assembly onto the distal electrode, the perforated, substantially insulating layer 36 results in an electrode with a much higher pacing impedance when compared to the pacing impedance from an electrode identically constructed but without this layer. This is a result of the perforation ratio, as previously defined, markedly reducing the effective area for current stimulation. The specific perforations are designed to result in localized areas of high current densities and high electrode pacing impedance. Devices of the present invention have perforations or apertures that result in pacing impedances ranging from about 1000 ohms to greater than about 10,000 ohms. Importantly, this high pacing impedance is achieved while still maintaining a large mechanical contact area 55. The large mechanical contact area 55 works to minimize the influence of lead placement and micro dislodgment on the stimulation threshold. The large mechanical contact area 55 also enables a large surface area for minimizing polarization artifacts during pacing stimulation. Devices of the present invention can have mechanical contact areas ranging from about 0.5 to 10 mm$^2$, with a preferred range of between about 1.5 and 5.0 mm$^2$.

Figure 4B:
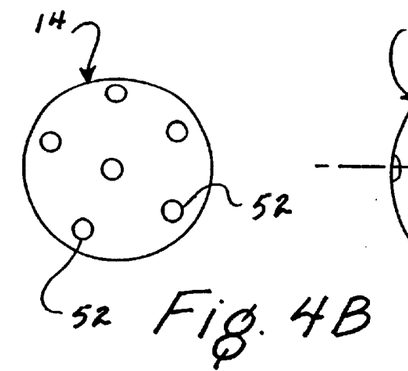
FIGS. 4B through 4G show end and side views of various hole or perforation patterns in the electrically insulating layer.
Figure 4C:
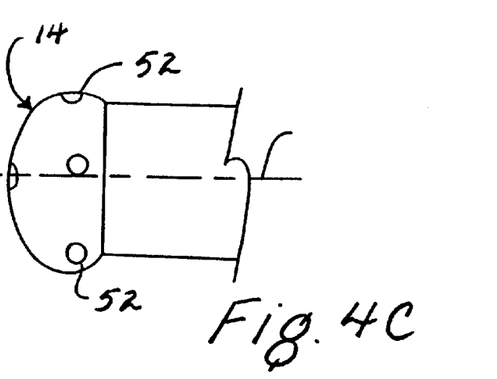
Figure 4D:
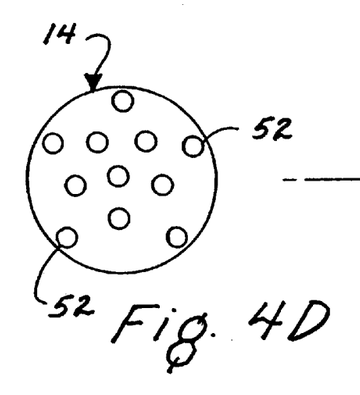
Figure 4E:
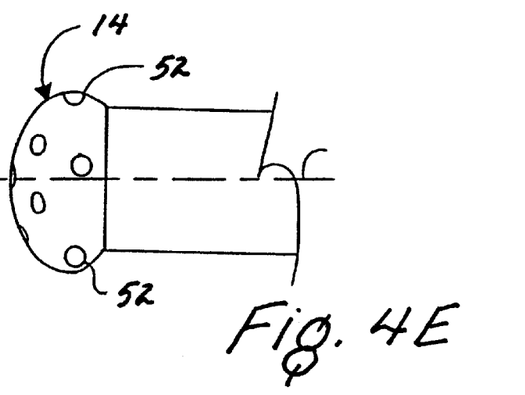
Figure 4F:
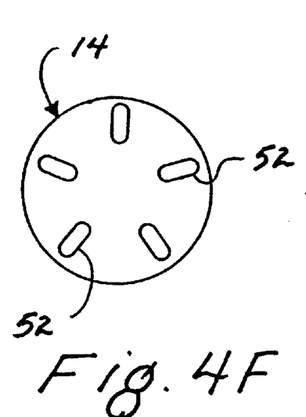
Figure 4G:
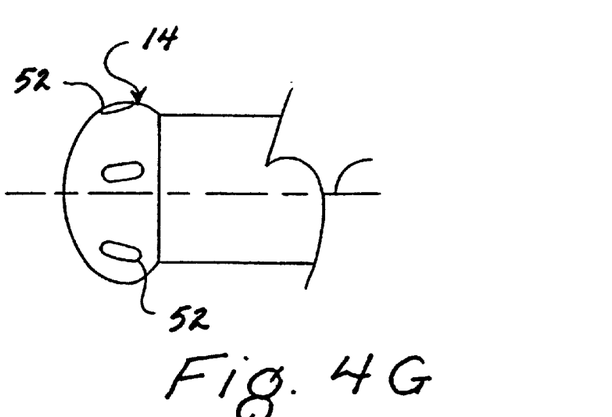

As shown in the end view of FIG. 4B and related side view of FIG. 4C describing a preferred embodiment, the distal electrode tip assembly 14 has six perforations or holes 52 in the electrically insulating layer wherein all six perforations are visible in the end view. When viewed perpendicular to the longitudinal axis 51, holes can be seen to be located both at the top of the hemisphere tip and down towards the area of the widest dimension. Other embodiments include other numbers of perforations 52, for example eleven, as shown in FIGS. 4D and 4E, and holes of a non-circular nature as shown in FIGS. 4F and 4G. Note that preferably, but not necessarily, the hole pattern has radial symmetry and is approximately aligned with the center of the longitudinal axis 51.

Figure 5:
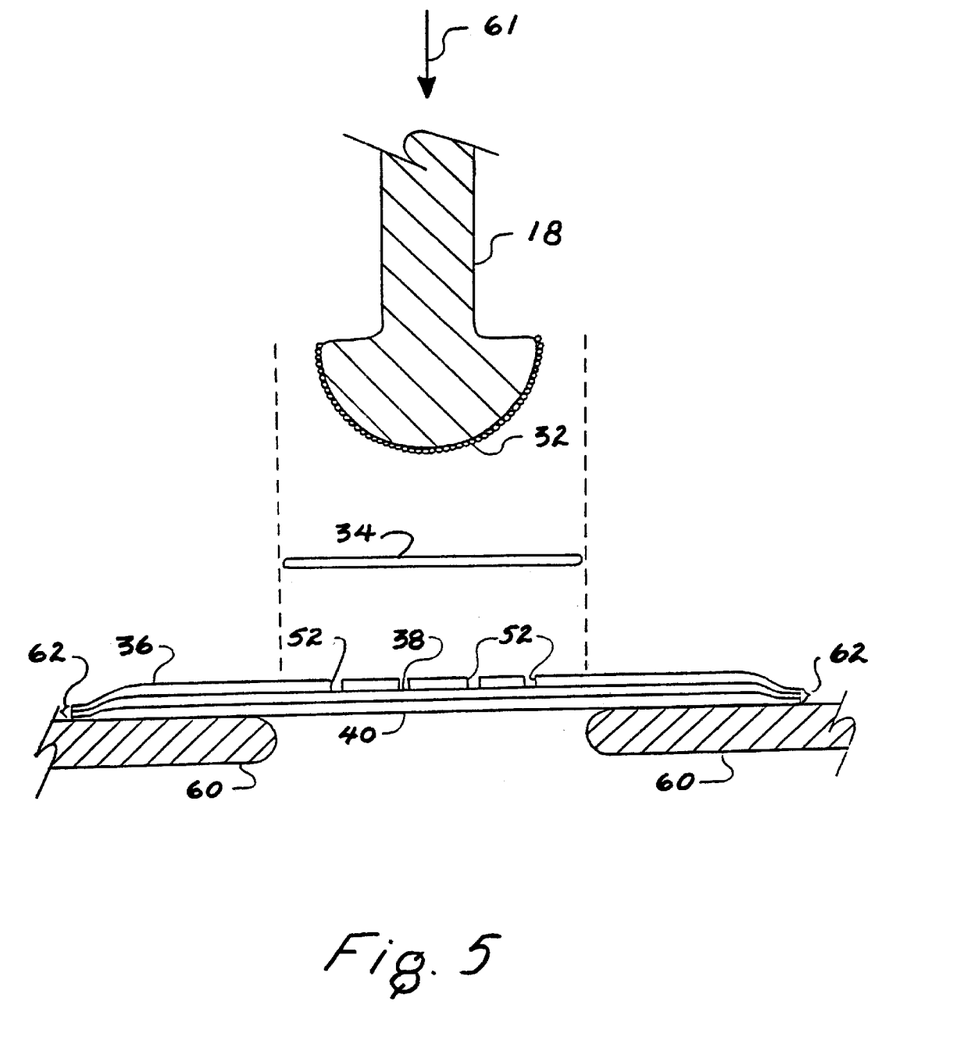
FIGS. 5 and 6 are cross-sections describing a method of assembling the multi-layer distal electrode.
Figure 6:
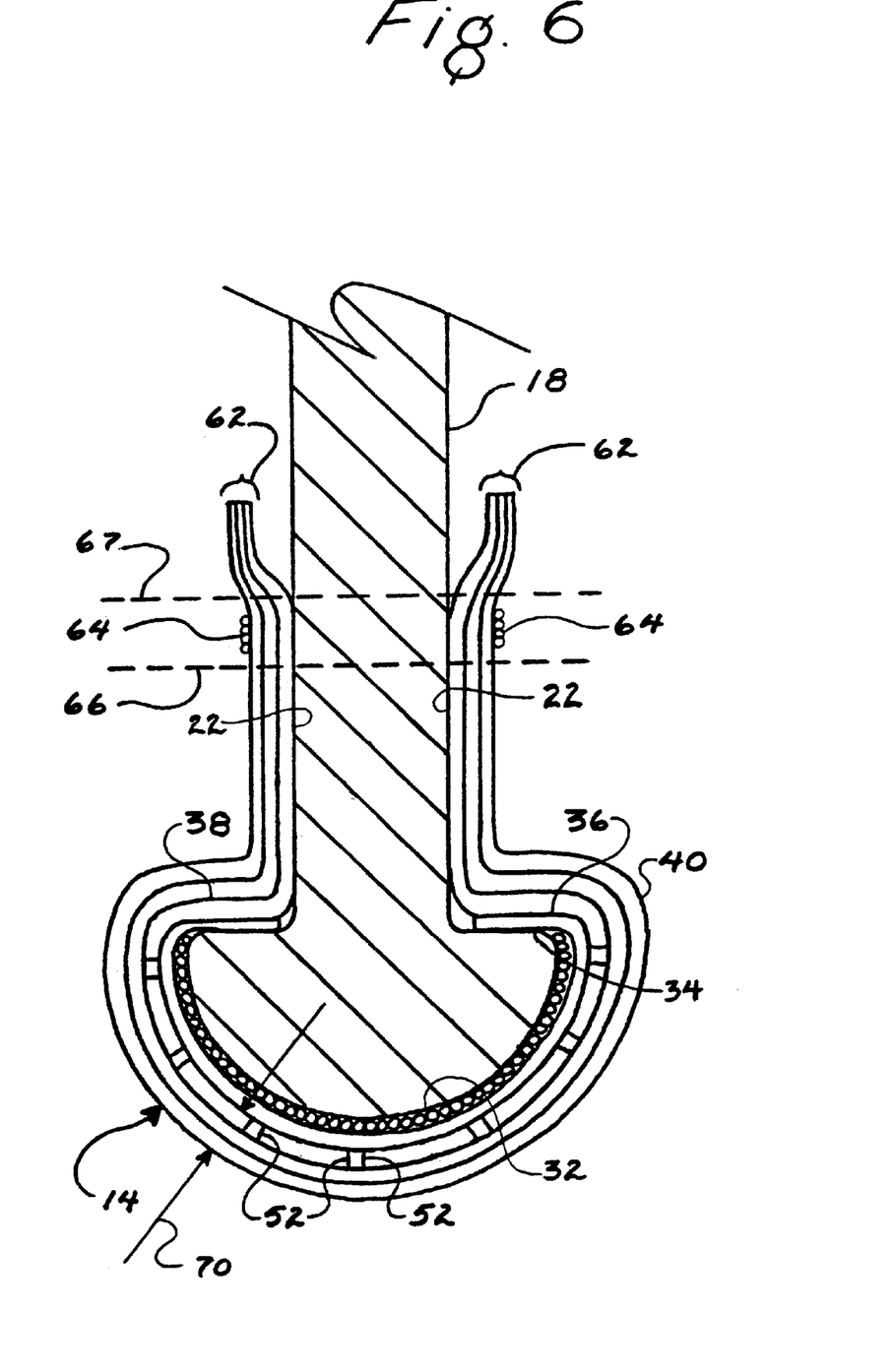

A preferred assembly method of the distal tip electrode is shown in FIGS. 5 and 6. The cell ingrowth layer 40 and the attached cell exclusion layer 38, are positioned onto an assembly fixture 60, as shown in FIG. 5. The perforated electrically insulating layer 36 is then positioned onto the cell exclusion layer 38. The three layers 36, 38 and 40 are then tacked together around an outer periphery by melting the electrically insulating layer 36, forming a bonded region 62. The electrically conductive material, preferred carbon filled ePTFE layer 34, is laser cut to size and then positioned onto the electrically insulating layer 36. The base electrode 18 with the sintered metal coating 32 is then positioned over the four layers 34, 36, 38 and 40 and pushed through the assembly fixture 60, along the axis 61. As shown in FIG. 6, the cell ingrowth layer 40, the cell exclusion layer 38 and the electrically insulating layer 36, extend over and beyond the sintered metal 32 portion of the base electrode 18. These three layers 36, 38 and 40 are then secured to the base electrode 18 by wrapping PTFE suture 64 (W.L. Gore and Associates, Flagstaff, Ariz.) around the three layers 36, 38 and 40 and the base electrode 18.

The assembly is then positioned onto a four jaw heat compression die (not shown) which compresses and thermally bonds the electrically insulating layer 36 in the attachment area 22. The three layers 36, 38 and 40 are then trimmed about an axis 67. Thus the electrically conductive material 18 and optional carbon-filled PTFE layer 34 are covered by one or more of layers or covers 36, 38 or 40. Optionally, the high temperature suture (or wire) 64 is removed, and the layers are trimmed about the axis 66. Referring to FIGS. 2A and 6, adhesive or additional thermoplastic bonding material 12, is placed between the three layers 36, 38 and 40, over the attachment area 22, and onto the exposed portion of the base electrode 18. The outer polymeric sleeve 8 is then positioned onto the base electrode 18 and over the three layers 36, 38 and 40 and placed into a four jaw heated compression die (not shown) and the adhesive or bonding thermoplastic 12 is melted in the attachment zone 22, thus bonding the outer polymeric sleeve 8 to the base electrode. As shown in FIG. 6, the outer three layers or covers 36, 38 and 40 have a thickness 70. In a preferred embodiment the thickness 70 of these three layers is less than 0.08 mm. In other embodiments this thickness 70 can be less than 0.09 mm, less than 0.1 mm, less than 0.15 mm or less than 0.25 mm. In a preferred embodiment, the thickness of the cell exclusion cover combined with the cell ingrowth cover is less than about 55 microns.

After implantation, the porous polymer layers become filled with body fluids. The ionic conductivity of the body fluids becomes part of the electrical path for the pacing stimulation and cardiac sensing functions. In a preferred embodiment, the polymer is an expanded PTFE structure that has been treated with a process so that the lead automatically or rapidly wets out upon contact with bodily fluids. Preferred processes that allow the electrode to automatically or rapidly wet out include the application of chemicals such as ducosate sodium (DSS) or polyvinyl alcohol (PVA).

Experimental results have been obtained from chronic canine animal studies of electrodes constructed per the present invention. In one such experiment, the distal stimulating electrode was constructed as shown in FIG. 3 with a Pt/Ir alloy base electrode item 18, sintered Pt/Ir metal micro spheres coated onto the base electrode item 32, Ketjen Black carbon-filled ePTFE conductive polymer layer item 34, FEP layer 36 with five perforation holes of a nominal diameter of 240 microns, and an ePTFE laminate layer item 38 and 40 for cell exclusion and cell ingrowth. The electrode was constructed as detailed in FIGS. 5 and 6. Prior to testing, the electrode was treated with a solution of PVA in order to aid in wetting of the microporous polytetrafluoroethylene by body fluids immediately following implantation. This was accomplished by submersing the ePTFE-covered electrode tip in isopropyl alcohol followed by submersion in 2% PVA/water solution. Next, the electrode tip is submersed in a 2% gluteraldehyde/1% hydrochloric acid solution in order to cross-link the PVA, followed by rinsing the electrode tip in sterile water to remove excess PVA.

Figure 7:
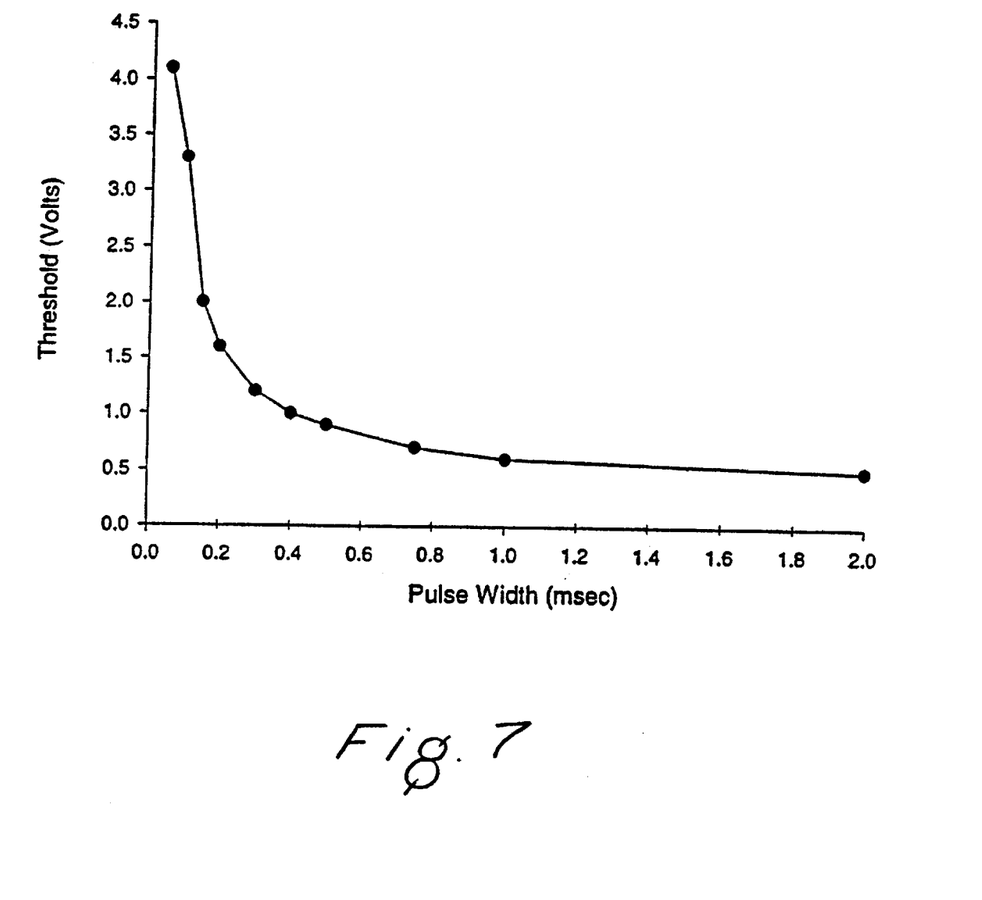
FIG. 7 is a graph showing the relation of threshold voltage vs. pulse width, at 35 days post implantation.

Acute data, collected via a Medtronic Model 5311B Pacing System Analyzer at time of implant deep in the right ventricular apex of a canine, showed a pacing voltage threshold of 0.2 volts (at 0.5 millisecond pulse width) and pacing impedance of 1373 ohms. Electrical performance data was collected intermittently throughout the 90 day study. During all data collections, the stimulation voltage, measured at 0.5 millisecond pulse width, was always less than 1 Volt and the pacing impedance was always greater than 1300 ohms. At day 90, the chronic stimulation voltage was 0.6 volts and the pacing impedance was 1515 ohms. Representative strength duration threshold data at 35 days post implantation is shown in FIG. 7. The pacing impedance measured 35 days post implantation was 1852 ohms.

The methodology for the determination of pacing impedance in an in vitro saline model is fully described in the standards document CEN/CENELEC Joint Working Group on Active Implantable Medical Devices (CEN/CLC JWG AIMD) Draft European Standard prEN 45502, part 2, section 6.2.1.3, "Determination of the unipolar pacing impedance". In brief, the lead and an indifferent electrode are inserted into a beaker of saline and connected to a signal generator set at an amplitude of 4.0 Volts and 0.5 millisecond pulse duration. The pacing impedance is computed by measuring the integral of the voltage waveform during the pacing impulse and dividing this by the integral of the current during the pacing impulse. The current is measured via the voltage across a series 10 ohm resistor. It is often useful to average the pacing impedance of 3–5 different leads in the determination of an electrode's pacing impedance.

The aforementioned Draft European Standard defines two test methods for the determination of the pacing impedance, one for a unipolar configuration and another for a bipolar configured lead or electrode. The pacing impedance of any electrode should be determined by the unipolar test using a second indifferent electrode. Thus for any type of electrode incorporating the embodiments of the present invention, the pacing impedance is defined as the calculated impedance value for a single, specific electrode, derived using the unipolar test with an indifferent electrode. For multi-channel or multi-conductor leads, only the electrode under consideration is tested using the unipolar test. The applicable sections of the aforementioned Draft European Standard are as follows:

6.2.1.1 Measurement of the Lead Conductor Resistance ($R_c$) and Lead Pacing Impedance ($Z_p$)

6.2.1.1 Test Conditions

The accuracy of appliances used for testing (oscilloscope, ohm-meter, resistor) must be 2 percent or better. The conductivity of the body is simulated during testing by a saline solution of 0.9 g/I±0.5% at a temperature of 37° C.±2° C. The Lead shall be removed aseptically from the Non-reusable Pack. The surface of a Lead with a porous structure shall not be allowed to dry out.

6.2.1.2 Determination of the Lead Conductor Resistance ($R_c$)

The Lead Conductor Resistance, ($R_c$), is measured by applying an ohm-meter between the Lead connector and the Electrode.

6.2.1.3 Determination of the Unipolar Lead Pacing Impedance ($Z_p$)

The Lead Pacing Impedance is determined by inserting the Lead into a beaker filled with the saline solution specified in subclause 6.2.1.1, so that the Electrode tip is placed approximately in the centre of the beaker (see FIG. 118). The indifferent Electrode of the pacing system is simulated by two metal plates of titanium placed according to FIG. 118. The dimensions of the beaker and the plates may be chosen linearly proportionally greater, but not smaller, than indicated in FIG. 118. Holes cut into the upper plate shall not reduce the total surface area by more than 10 percent.

The Lead and the parallel circuit formed by both plates are connected to a test signal generator that is adjusted to produce a pulse that has a duration of 0.5 ms±0.05 ms and an amplitude of 4 V±0.1 V. The current, I, is determined by measuring the voltage drop across the 10 ohm±2% resistor. The mean values of voltage and current are used for determination of the Lead Pacing Impedance by applying the following formula:

$$Z_{UNI} = \frac{\int U dt}{\int I dt} = 10\Omega * \frac{\int U_1 dt}{\int U_2 dt}$$

Figure 8:
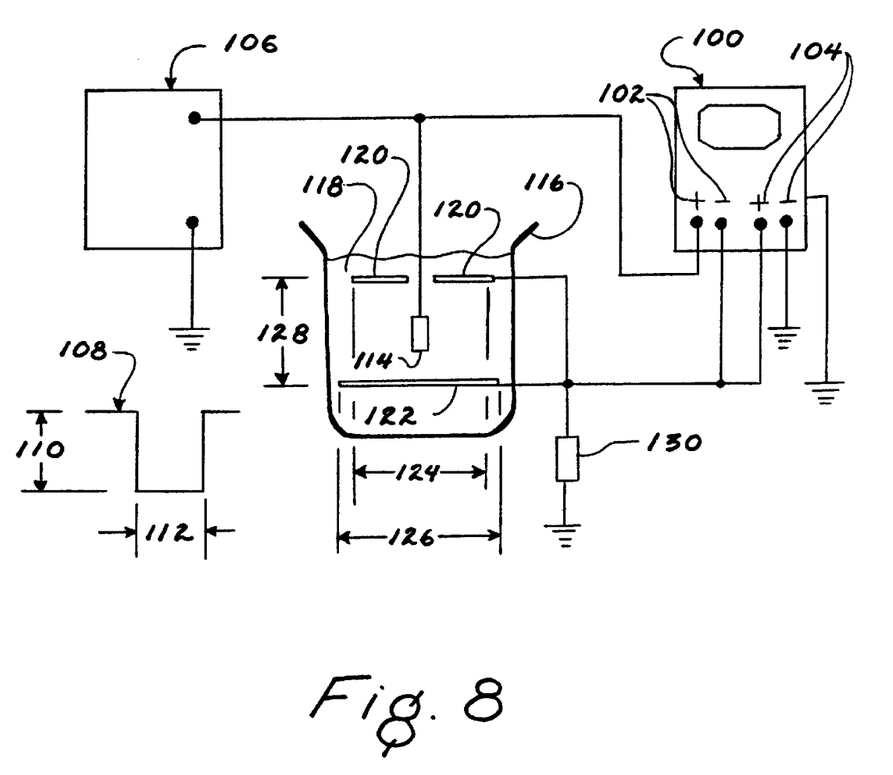
FIG. 8 is a schematic drawing of the test apparatus used for determining the electrode impedance and the post pacing polarization artifact.

FIG. 118, referred to above in the Draft European Standard, is shown herein as FIGS. 8. FIG. 8 depicts FIG. 118 of the Draft European Standard, which applies to a unipolar lead. As shown in FIG. 8, an oscilloscope 100 has two channels U1 102 and U2 104. A test signal generator 106 produces a output wave form 108, having an amplitude 110 and a pulse duration 112. The pulse amplitude 110 is 4.0 volt±0.1 volt and the pulse duration 112 is 0.5 ms±0.05 ms. The electrode tip 114 is placed into the approximate center of the beaker 116, which is filled with saline solution 118. In the beaker 116 are two titanium plates, a top plate 120 and a bottom plate 122. The top plate has a width 124 of at least 40 mm and the bottom plate has a width 126 of 50 mm. The two plates 120 and 122 have a vertical separation distance 128 of 60 mm. The resistor 130 has a value of 10 ohms±2%.

The methodology for the determination of post pacing polarization artifact follows the same setup described above (Draft European Standard prEN 45502, part 2, section 6.2.1.3). The post pacing artifact is measured with an oscilloscope. The measurement is made 30 milliseconds following the pacing pulse and with the signal generator set at 4.0 Volts and 0.5 millisecond pulse duration. One applicable signal generator that can be used for this measurement is a Medtronic Model 5311B Pacing System Analyzer. This signal generator mimics the voltage waveform both during and shortly after the pacing stimulus that is typically generated by a pacemaker. The post pacing polarization artifact measurement determines the residual voltage shortly after pacing stimulation. Electrodes with large polarization artifact measures are both less efficient and can present problems to the pacemaker in sensing the following heart activity when compared to electrodes with small polarization artifact measures. It is often useful to average the post polarization artifact of 3–5 different leads in the determination of an electrode's post polarization artifact. Devices of the present invention typically have post pacing polarization artifact voltages of less than 20 millivolts.

The in vivo chronic stimulation voltage is determined by setting the pacing stimulus generator to a pulse duration of 0.5 millisecond and an elevated pulse amplitude. The in vivo threshold voltage can be determined in either the clinical human or in an animal model (preferably canine). The lead position is ideally deep in the right ventricular apex and fluoroscopic imaging can be used to verify both the correct position and the possibility of lead dislodgement. Situations of lead dislodgement, a known complication of this type of therapy, are excluded in determination of an electrode's threshold performance. Following determination that the pacing is capturing the heart, the stimulus amplitude is slowly reduced. When myocardial capture fails (as detected by a drop in heart rate and a change in QRS morphology using a surface ECG monitor) the last voltage that maintained consistent capture is noted. Consistent capture is the voltage level that maintained approximately 100% captured paced beats for a period of 5 seconds or longer. This voltage is defined as the voltage threshold and is the chronic voltage threshold if the electrode has been implanted for a duration greater than 30 days. It is often useful to average the in vivo threshold voltage of 3–5 different leads in the determination of an electrode's in vivo threshold voltage.

Although it will become evident to those skilled in the art that the present invention is applicable to a variety of implantable medical devices utilizing pulse generators to stimulate selected body tissue, the invention and its background has been described principally in the specific example of cardiac pacemakers used to provide precise stimulation pulses to the heart. While the present invention has been described as a unipolar electrode, other embodiments are possible such as applications to bipolar electrode leads or any stimulating or sensing electrode device in an annular or planer configuration. The appended claims are not intended to be limited to any specific example or embodiment herein described.

We claim:

1. An electrode comprising:
    a) an electrically conductive material;
    b) a layer of substantially electrically insulating material having at least one aperture therethrough, said layer of substantially electrically insulating material covering the electrically conductive material; and
    c) a microporous cover over the at least one aperture.
2. An electrode according to claim 1 wherein the electrode provides a pacing impedance of greater than about 1000 ohms.
3. An electrode according to claim 2 wherein the electrode provides a chronic stimulation voltage threshold of less than about 5.0 volts.
4. An electrode according to claim 1 wherein the electrode provides a chronic stimulation voltage threshold of less than about 5.0 volts.
5. An electrode according to claim 4, wherein the electrode maintains the chronic stimulation voltage without the use of steroid elution.
6. An electrode according to claim 1, wherein the electrode further provides a post pacing polarization artifact of less than about 20 millivolts.
7. An electrode according to claim 1, wherein the microporous cover is a polymer.
8. An electrode according to claim 7, wherein the polymer is a fluoropolymer.
9. An electrode according to claim 8, wherein the fluoropolymer is porous polytetrafluoroethylene.
10. An electrode according to claim 1, wherein the microporous cover has a thickness of less than about 0.055 mm.
11. An electrode according to claim 1, wherein the microporous cover has a thickness of less than about 0.15 mm.
12. An electrode according to claim 1, wherein the microporous cover has a thickness of less than about 0.25 mm.
13. An electrode according to claim 1, wherein the electrode provides a pacing impedance of greater than about 5000 ohms.
14. An electrode according to claim 1, wherein the electrode provides a pacing impedance of greater than about 10,000 ohms.
15. An electrode according to claim 1 wherein the microporous cover has been treated with polyvinyl alcohol prior to implantation in a living body.
16. An electrode according to claim 15 wherein the microporous cover comprises porous polytetrafluoroethylene.
17. A stimulation system comprising a stimulator and an electrode according to claim 1.
18. An electrode according to claim 1 wherein the microporous cover comprises a cell exclusion layer covering the at least one aperture and substantially preventing cellular ingrowth into the at least one aperture.
19. An electrode according to claim 18, wherein the cell exclusion layer comprises porous polytetrafluoroethylene.
20. An electrode according to claim 19 wherein a cell ingrowth layer covers the cell exclusion layer.
21. An electrode according to claim 20 wherein the cell ingrowth layer comprises porous polytetrafluoroethylene.
22. An electrode according to claim 18 wherein a cell ingrowth layer covers the cell exclusion layer.
23. An electrode according to claim 22 wherein the cell ingrowth layer comprises porous polytetrafluoroethylene.
24. An electrode according to claim 22 wherein the thickness of the cell ingrowth layer and the cell exclusion layer is less than about 0.08 mm.

25. An electrode according to claim 22 wherein the thickness of the cell ingrowth layer and the cell exclusion layer is less than about 0.15 mm.

26. An electrode according to claim 22 wherein the thickness of the cell ingrowth layer and the cell exclusion layer is less than about 0.25 mm.

27. An electrode according to claim 1 wherein the at least one aperture comprises multiple apertures.

28. An electrode according to claim 1 wherein the microporous cover comprises a cell exclusion layer covering the at least one aperture.

29. An electrode according to claim 1 wherein the substantially electrically insulating material is non-porous and surrounds the at least one aperture, and the at least one aperture has an opening with an area of less than about 0.09 mm$^2$.

30. An electrode according to claim 1 wherein the electrically conductive material is a carbonized polymer.

31. An electrode according to claim 30, wherein the carbonized polymer comprises a fluoropolymer.

32. An electrode according to claim 31, wherein the fluoropolymer is porous polytetrafluoroethylene.

33. An electrode according to claim 1, wherein the electrically conductive material covers a conductive metal element.

34. An electrode comprising:
a) an electrically conductive material; and
b) a layer of substantially electrically insulating material covering a surface of the electrically conductive material, the layer having at least one aperture therethrough exposing a portion of the surface of the electrically conductive material, wherein the at least one aperture contains a microporous material that covers the portion of the surface of the electrically conductive material, said microporous material having interconnected void spaces such that the at least one aperture is permeable to electrically conductive liquids.

35. An electrode according to claim 34 wherein the substantially electrically insulating material is non-porous and surrounds the at least one aperture, and the interconnected void spaces are sized appropriately to substantially prevent cellular ingrowth.

36. An electrode according to claim 35 wherein the layer of substantially electrically insulating material is provided with a microporous cover having void spaces therein of a size appropriate to allow cellular ingrowth.

37. An electrode according to claim 34 wherein the layer of substantially electrically insulating material is provided with a microporous cover having void spaces therein of a size appropriate to allow cellular ingrowth.

38. An electrode according to claim 37 wherein the at least one aperture comprises multiple apertures.

39. An electrode according to claim 34 wherein the at least one aperture comprises multiple apertures.

40. An electrode comprising:
a) an electrically conductive material;
b) a microporous cell exclusion layer covering the electrically conductive material, said microporous cell exclusion layer having void spaces therein of a size appropriate to substantially prevent the ingrowth of cells; and
c) a microporous cell ingrowth layer covering a substantial portion of the microporous cell exclusion layer, said microporous cell ingrowth layer having void spaces therein of a size appropriate to allow cellular ingrowth.

41. An electrode comprising:
a) an electrically conductive material;
b) a layer of substantially electrically insulating material covering the electrically conductive material, said layer of substantially electrically insulating material being non-porous and having a multiplicity of holes therethrough wherein each of said holes has an area of about 0.09 mm$^2$ or less; and
c) a microporous cover over the layer of substantially electrically insulating material.

42. An electrode comprising:
a) an electrically conductive material;
b) a layer of electrically conductive material of high surface area covering the electrically conductive material;
c) a layer of substantially electrically insulating material covering the layer of electrically conductive material of high surface area, said layer of electrically insulating material having at least one aperture therethrough;
d) a microporous cell exclusion layer covering the layer of electrically insulating material, said microporous cell exclusion layer having void spaces therein of a size appropriate to substantially prevent the ingrowth of cells; and
e) a microporous cell ingrowth layer covering a substantial portion of the microporous cell exclusion layer, said microporous cell ingrowth layer having void spaces therein of a size appropriate to allow cellular ingrowth.

43. An electrode according to claim 42 wherein the layer of electrically conductive material of high surface area comprises an electrically conductive porous polymer.

44. An electrode according to claim 43 wherein the electrically conductive porous polymer is porous polytetrafluoroethylene.

45. An electrode according to claim 42 wherein the layer of substantially electrically insulating material is fluorinated ethylene propylene.

* * * * *